United States Patent [19]

Mezei et al.

[11] Patent Number: 4,586,546

[45] Date of Patent: May 6, 1986

[54] LIQUID HANDLING DEVICE AND METHOD

[75] Inventors: Louis M. Mezei, Fremont; Richard W. Reeves, San Rafael; Richard A. Leath; Joseph T. Widunas, both of Berkeley, all of Calif.

[73] Assignee: Cetus Corporation, Emeryville, Calif.

[21] Appl. No.: 663,882

[22] Filed: Oct. 23, 1984

[51] Int. Cl.⁴ .............................................. B65B 3/04
[52] U.S. Cl. ............................................ 141/2; 141/67; 73/864.24; 422/100; 436/180
[58] Field of Search ................................... 141/18–29, 141/67, 1–12; 73/864.24, 864.25, 864.01; 422/100; 436/180

[56] References Cited

U.S. PATENT DOCUMENTS

| | | | |
|---|---|---|---|
| 3,635,094 | 1/1972 | Oberli | 73/864.24 |
| 3,894,438 | 7/1975 | Ginsberg | 73/864.24 |
| 3,915,651 | 10/1975 | Nishi | 23/259 |
| 4,276,260 | 6/1981 | Drbal et al. | 422/100 |
| 4,331,262 | 5/1982 | Snyder et al. | 222/37 |
| 4,345,483 | 8/1982 | Paletta et al. | 73/864.16 |
| 4,399,711 | 8/1983 | Klein | 73/864.16 |
| 4,475,666 | 10/1984 | Bilbrey et al. | 222/14 |

OTHER PUBLICATIONS

Megargle et al., *Chemical Instrumentation*, 4, 29 (1972).

*Primary Examiner*—Houston S. Bell, Jr.
*Attorney, Agent, or Firm*—Albert P. Halluin; Peter J. Dehlinger; Ronald C. Fish

[57] ABSTRACT

An improved liquid handling device used for transferring a selected quantity of liquid from one receptacle to another. The device includes a meniscus tracking feature which minimizes mixing in a liquid sample and contact between the sample and a sample-handling pipette during a liquid-transfer operation. Further included is a volume-correcting feature for improving the accuracy of volume withdrawn into or dispensed from the pipette during a liquid handling operation.

13 Claims, 10 Drawing Figures

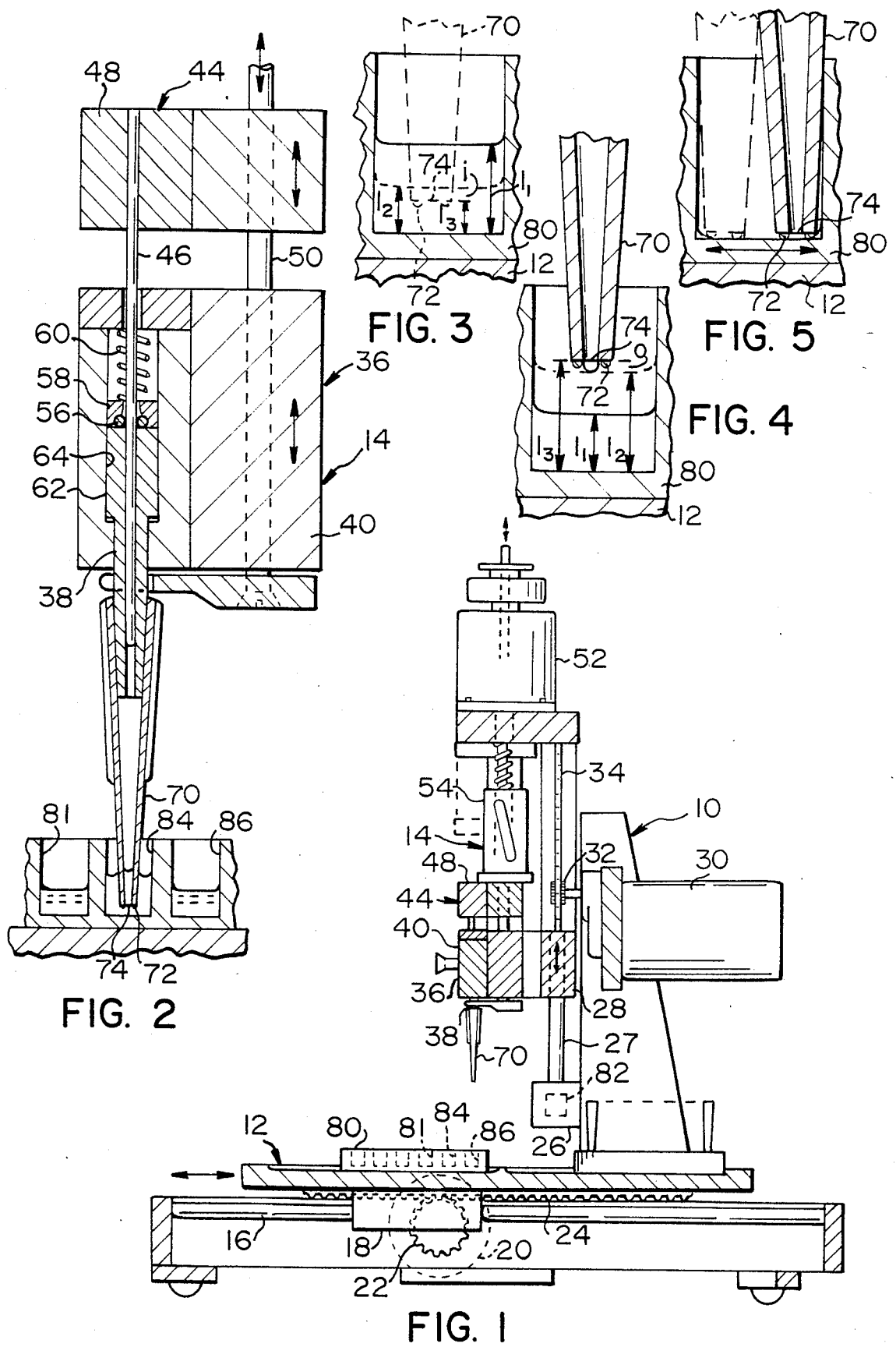

LIQUID HANDLING DEVICE AND METHOD

BACKGROUND AND SUMMARY

The present invention relates to liquid handling devices, and in particular, to improvements therein for increasing the accuracy of liquid volumes which are transferred by the device.

A number of screening and/or assay procedures in the biochemical field rely on transfer of small liquid volumes from one receptacle to another. For example, in screening monoclonal antibody cell lines, small-volume samples are removed from each of a plurality of cell microcultures and transferred to individual receptacles where antibody activity is assayed. Another common procedure relies on serial dilution of analyte samples, by successive transfer of small sample volumes from one diluent receptacle to another, for assaying the analyte.

Automated liquid handling machines for performing small-volume liquid transfers have been developed. U.S. patent application for "Liquid Sample Handling System", Ser. No. 456,974, filed Jan. 21, 1983, now U.S. Pat. No. 4,502,831 and assigned to the assignee of the present invention, describes an automated liquid handling system which is capable of performing serial dilutions, automatically and simultaneously, on a plurality of samples. The system includes a vertically shiftable head assembly which supports a plurality of liquid-transfer pipettes, and a horizontally shiftable table which supports one or more receptacle trays. In operation, the table is shifted to place a row of receptacles in a tray directly below the pipettes, and the head assembly is lowered to position the pipettes in corresponding receptacles. To withdraw a selected quantity of liquid from each receptacle, a series of plungers, one associated with each pipette, is moved coordinately in an upward direction by a digitally controlled stepper motor also mounted on the head assembly. The head assembly is now raised and the table shifted to position a second row of receptacles directly below the pipettes. The head assembly is again lowered, to place the pipettes within the corresponding receptacles in the second row, and the stepper motor controlling the plungers is operated in a downward direction to dispense the samples into the receiving receptacles.

Liquid handling systems of the type described ideally are able to transfer selected volumes in the range typically between about 2 and 200 $\mu$l. However, experience has shown that the system may seriously underfill at small volumes, i.e., between about 2 and 20 $\mu$l. There appear to be at least two factors contributing to sample underfill. One is play or slack in the mechanical linkage between the plunger mechanism and the stepper motor which moves this mechanism. The slack is intensified by the drag placed on the system by friction between the seals within the pipettes. These effects can produce a considerable differential in the distances travelled by the support when the stepper motor is driven in one direction and when it is driven in the opposing direction. A second contributing factor is inherent in pipettes that function by induced internal-volume pressure changes. Here volume uptake tends to be non-linear in the low-volume (low pressure differential) range, and can also vary significantly with different liquid viscosities.

Another source of volume-transfer error in automated liquid handling device, such as the one described above, is the tendency of small beads of liquid to cling to the inside and outside of the pipette tips, or enter the tips by capillarity during a liquid transfer operation. The excess sample material clinging to the pipette tips is also undesirable in that the material may fall into adjacent receptacles during liquid handling and cause contamination of samples.

It is one general object of the invention, therefore, to provide an improved liquid handling device which substantially overcomes the above-discussed volume-accuracy and contamination problems associated with the prior art.

A more specific object of the invention is to provide in such a device, a meniscus-tracking feature which is operable to place pipettes in the system at a level which minimizes the tendency of sample material to cling to the pipette tips.

Another object of the invention is to provide in such a device a volume-correction feature which is operable to transfer liquid volumes accurately over an extended volume range, preferably between about 2 and 200 $\mu$l.

The invention includes an improved automatic liquid handling device of the type having a pipette tip whose lower end is moved by vertical shifting into a receptacle, to allow a preselected quantity of liquid in the receptacle to be withdrawn from or dispensed into the receptacle. One aspect of the invention is a meniscus-tracking feature by which such vertical shifting is controlled to position the tip's lower end at a selected level in the receptacle. This level is less than about 100 mils from the liquid meniscus which results when a selected quantity of liquid is withdrawn from or dispensed into the receptacle.

Another aspect of the invention is a volume-correction feature for reducing the difference between the actual and specified sample volumes transferred by the device, particularly at relatively low and relatively high handled volumes. The volume-correction feature operates by approximating the actual amounts of liquid dispensed, at different specified volumes, by a polynomial expression, and adjusting the actual volumes dispensed according to the slope and intercept of the expression.

These and other objects and features of the invention will become more fully apparent when the following detailed description of the invention is read in conjunction with the accompanying drawings.

BRIEF DESCRIPTION OF THE DRAWINGS

FIG. 1 is a side sectional view of a liquid handling device incorporating the improved features of the invention;

FIG. 2 is an enlarged side sectional view of a portion of the device showing the device in a position for pipetting liquid into or out of a receptacle;

FIG. 3 is an enlarged side view of a receptacle region seen in FIG. 2, with a pipette in the device positioned for withdrawing a selected quantity of liquid from the receptacle;

FIG. 4 is a view like FIG. 3, showing the pipette positioned for dispensing a selected quantity of liquid into a receptacle;

FIG. 5 is a view like FIGS. 3 and 4, showing relative movement between the pipette tip and a receptacle to allow substantially complete removal of the sample in the receptacle;

DETAILED DESCRIPTION OF THE INVENTION

Figure 6:
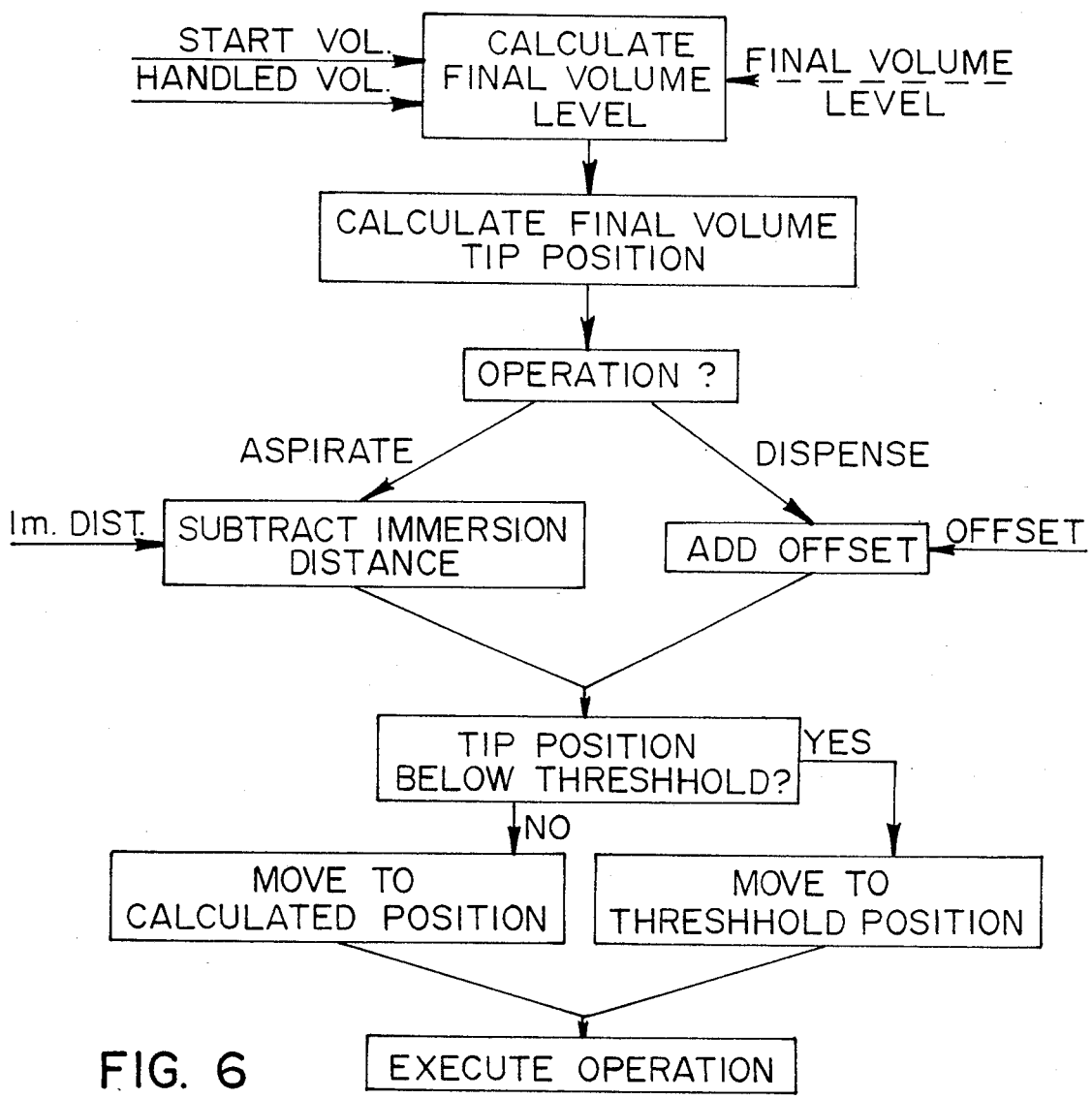
FIG. 6 is a flow diagram showing the operation of a meniscus-tracking feature which forms part of the invention.
Figure 7:
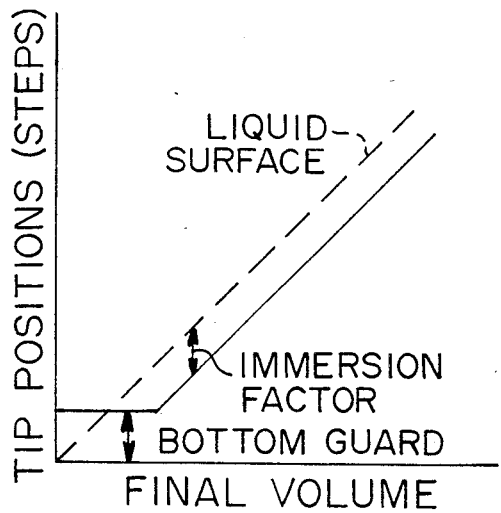
FIGS. 7 and 8 are plots showing the position of a pipette tip as a function of stepper motor steps, in relation to final liquid surface levels in liquid withdrawal and liquid dispensing operations, respectively.

FIG. 1 shows an automated liquid handling device 10 incorporating the novel features of the present invention. The device includes two main moveable parts, a horizontally translatable table 12 and a vertically translatable head assembly 14. The table is mounted for horizontal translation on hardened guide rods 16 by means of slide bearings 18. Translation of the table is provided by a stepper motor 20 through a pinion 22 connected to the motor and a rack 24 mounted on the underside of the table. The stepper motor is actuated for movement in a selected direction, over a given arcuate distance, by a series of digitized impulses which are supplied to the motor from an electronic control unit 26. Movement of the table under the control of unit 26 will be described below.

Similarly, assembly 14 is mounted for vertical translation on guide rods 27 by means of slide bearings 28. Translation of the head assembly is provided by a stepper motor 30 mechanically linked to the assembly through a pinion 32 and rack 34. Stepper motor 30, like motor 20, is actuated by digitized impulses from unit 26, to advance the motor in a selected direction over a given arcuate distance, to provide accurate control of the movement of the head assembly. Novel operational features of unit 26 and its operation with regard to positioning the head assembly in accordance with the present invention will be detailed below. Motor 30, and the rack and pinion mechanical linkage between the motor and head assembly are also referred to herein, collectively, as shifting means.

With continued reference to FIG. 1, head assembly 14 supports a pipette assembly 36 which includes a series of pipettes, such as pipette 38, arranged in a row extending transverse with respect to the axis of translation of table 12, i.e., in the direction normal to the plane of FIG. 1. Typically, there are eight such pipettes equally spaced over a total distance of about four inches. The pipettes are attached to the head assembly by means of a mounting block 40. Also included in the pipette assembly is a plunger mechanism, or a means 44 which is mounted on the head assembly for vertical movement relative to the pipettes. The plunger mechanism includes a series of plunger rods, one for each pipette, such as rod 46 in pipette 38. The rods are mounted on a common actuator bar 48 which itself is slideably mounted on a pair of guide rods, such as guide rod 50, for vertical shifting under the control of a stepper motor 52 (FIG. 1). The motor is mechanically linked to the actuator bar through a ball screw drive mechanism 54. Actuation of motor 52 is under the control of digitized impulses supplied from unit 26, in accordance with a novel operational features of the unit which is to be described. As seen best in the enlarged sectional view in FIG. 2, translation of the plunger rods under the control of motor 52 changes the internal volume of the pipettes, causing fluid to be aspirated into or expelled from pipettes.

Considering the detailed description of pipette 38, which is representative, an airtight seal is (FIG. 2) provided between rod 46 and the top of the pipette by means of a ball seal 56 held in place by a grommet 58 and a compliance spring 60. The pipette has a piston section 62 which is reciprocably mounted in a cylinder 64 formed in the mounting block. The spring-bias pipette support construction accomodates relative vertical movement among the several pipettes, which may occur at certain phases of a normal liquid-handling operation.

With continued reference to FIG. 2, the lower end region of the pipette is tapered on its exterior surface so as to received and frictionally engage the inner surface of a disposable pipette tip 70 which itself has the tapered construction shown in FIGS. 2-14 5. The tip is preferably constructed of a hydrophobic (e.g., surfactants make wettable) polymeric material such as polypropylene. The tip volume is such as to readily accommodate a liquid transfer operation involving volume in the range of about 2-200 $\mu$l, and, as seen in FIG. 2, makes up a substantial portion of the volume of the cylinder formed by the barrel of pipette 38 and the interior volume of the tip. The lower end of the tip is provided with a tip guard 72 which limits movement of the tip into a flat-bottomed receptacle to a position where the lower open end 74 of the tip is spaced a precise distance from the bottom of the receptacle. The guard is preferably constructed to prevent movement of the tip's lower end closer than about 2 mils from the bottom of the receptacle.

The liquid samples which are transferred during an operation of device 10 are normally contained in multi-well trays, such as tray 80, seen in FIG. 1. Receptacles 81, 84, 86 seen in sectional view in FIG. 1, are members of a rectangular array of receptacles in the tray. The wells in tray 80 are preferably constructed, for example by conventional molding techniques, as flat-bottom cylindrical wells whose total volume is preferably about twice the maximum volume which can be handled by the pipettes, allowing a pipette to be inserted into a fully loaded receptacle without displacing liquid therefrom. For example, where the maximum liquid volume handled by the pipette is 200 $\mu$l, the wells have a typical volume capacity of 400 to 500 $\mu$l. The cylindrical diameter of each well is, as shown, substantially greater than that of the inserted portion of the tip, allowing the tip to be moved to off-center positions within the receptacle, to place the tip's lower end near lower side regions of the receptacle, as will be described below with reference to FIG. 5. Suitable receptacles for use in the present invention include, in addition to the cylindrical tray wells just described, any suitable sample receptacle, such as round-bottom tray wells, or round or flat-bottom tubes that can be supported in a fixed manner on table 12.

The description of the mechanical features of device 10 herein has been limited to those features which are important for an understanding of the present invention. In this regard, it is noted that the liquid handling device, in its simplest embodiment, may include a single pipette assembly of the type described (including, e.g., an x-y assembly), and shifting means for moving the lower end of the pipette tip into a receptacle, to allow a preselected quantity of liquid in a receptacle to be withdrawn from or dispensed into the receptacle.

Unit 26, which controls operation of device 10 in accordance with the novel features of the present invention, will now be considered. The basic component of the control unit is a microprocessor 82 which functions as a pulse generator to control the sequence of operations of motors 20, 30 and 52 to effect desired sequential movements of table 12, head assembly 14, and the plunger mechanism 44 during a liquid-handling operation. For purposes of explaining the operational control features of the microprocessor, the control provided to each of the three motors during the course of a liquid-handling operation will be separately considered, first with reference to motor 30 in head assembly 14.

In an operation for transferring a liquid sample from one receptacle to another, the head assembly is first lowered to position the pipette tip in a corresponding receptacle in the tray. After a preselected quantity of liquid has been withdrawn from the receptacle, the head assembly is raised to permit horizontal shifting of the tray to position another receptacle below the pipette. The assembly is now lowered into the newly positioned receptacle and the withdrawn material is dispensed. It is noted that the movement, positioning and operation being described with reference to pipette 36 may be occurring simultaneously in all of the pipettes in device 10.

According to an important feature of the present invention, the head assembly is moved, immediately prior to the liquid withdrawal and liquid dispensing steps, to position the lower end of the pipette near the liquid meniscus which results from the liquid withdrawal or dispensing step. Explaining further, to withdraw a preselected quantity of liquid from a receptacle, the head assembly is moved to position the pipette tip near the level of liquid in the receptacle which remains after the preselected quantity has been removed. Preferably the pipette tip is positioned about 100 mils or less below the resulting meniscus, to ensure that the lower end of the tip remains immersed during liquid withdrawal. Similarly, in a liquid dispensing step, the head assembly is moved to position the lower end of the pipette tip at or close to the meniscus which will result in the receptacle after the liquid has been dispensed. Preferably, in the dispensing step, the lower end of the pipette tip is placed above the liquid meniscus, within about 100 mils thereof, at a position which will allow "a drip" on the pipette tip end to be drawn off by contact with the sample surface.

FIG. 6 shows, in flow-diagram form, the steps carried out by microprocessor in executing the above-described positioning operations. As indicated at the top of the figure, input information concerning the original or "start" liquid volume in the receptacle and the handled volume—meaning the volume which is to be withdrawn from or dispensed into the receptacle—is used to calculate a final liquid volume. The inputted volume information, which is stored in a volatile memory in the microprocessor, is converted by the microprocessor to a final-volume level position based on the known volume/height characteristics of the receptacle which, for at least one standard-sized receptacle used in the device, are stored in a permanent memory in the microprocessor. When the liquid-handling operation is carried out in "non-standard" receptacles, the microprocessor may be supplied directly with a final-volume level determined empirically by the user, as indicated by the dashed input line at the upper box in the diagram.

The final-volume level is used to calculate a final-volume meniscus tip position—that is, the position at which the tip's lower end is on the final-volume meniscus—by means of a linear relationship between liquid surface level and the number of steps of stepper motor 30 which are required to produce a given change in tip position. This relationship is indicated by the dashed line in the graph in FIG. 7, and is based on a zero-step/zero-volume initial position, where an increasing number of steps produces movement away from the bottom of the receptacle, as determined by the slope of the dotted line.

As indicated above, in an aspiration or withdrawal step, the tip position is placed slightly below the final-volume meniscus to insure that the tip remains immersed as liquid is withdrawn from the receptacle. This immersion distance, or factor is preferably between about 10 and 100 mils and more preferably between about 20 and 50 mils and is selected by the user. The inputted immersion distance is subtracted from the above-calculated final volume tip position to yield a calculated tip position which is indicated in solid line in FIG. 7. As shown, the calculated tip position has a lower threshold level at which the bottom guard in the tip makes contact with he lower bottom of the receptacle. The flow chart indicates that, above and below the threshold level, the tip is moved to the calculated tip position and the threshold position, respectively. The microprocessor then supplies motor 30 with the calculated number of steps to position the tip's lower end at the calculated final position and the aspiration operation is executed.

Figure 8:
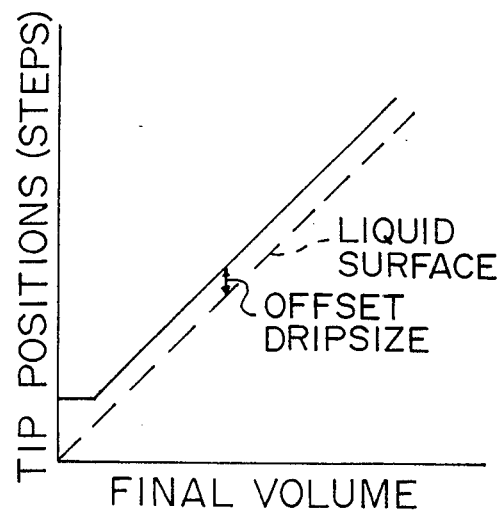

Similarly, in a dispensing operation, an offset distance, typically between about 10 and 50 $\mu$l is inputted into the volatile memory of the microprocessor and added, as indicated in the flow chart, to the calculated final-volume tip position. After the pipette assembly is moved to the calculated position, under the control of the microprocessor, the liquid dispensing operation is executed as indicated in the flow diagram. The position of the tip, in relation to the liquid surface level, is shown in FIG. 8.

The electronic processing elements of the microprocessor which are dedicated to carrying out the data processing shown in the flow diagram in FIG. 6 are also referred to herein as circuit means. The circuit means operates to determine, from information concerning the initial and handled volumes in a receptacle, and the amount of pipette tip immersion and offset, the number of digitized impulses to be supplied to stepper motor 30 for positioning the tip's lower end at the desired level in the receptacle. The circuit means, and an associated pulse generator in the microprocessor which supply the calculated number of digitized impulses to the stepper motor, are also referred to herein, collectively, as positioning means. The construction and programming of a microprocessor to produce such positioning means would be known to one skilled in the art.

The operation of the meniscus-tracking feature just described can be appreciated readily from FIGS. 3 and 4. In FIG. 3, a receptacle from which a given volume of sample is to be withdrawn initially contains a sample volume whose meniscus level is a distance $l_1$ above the bottom of the receptacle, where the bottom of the receptacle is taken as the zero-point position on the graph in FIG. 7. This initial volume level is determined from the known amount of liquid in the receptacle and the receptacle volume characteristics as described above. The dotted meniscus line in FIG. 3 represents the liquid meniscus level which is produced after the selected quantity of liquid sample has been removed from the receptacle. As seen, this level is a distance $l_2$ above the zero-point line. The immersion distance, represented by i in the figure, is subtracted from $l_2$ to produce a calculated distance of $l_3$ above the zero-point line at which the lower end of the pipette will be positioned in the liquid-withdrawing step.

The liquid-meniscus tracking feature provides two important advantages in a liquid aspiration step. First, in a number of important applications such as screening procedures for identifying monoclonal antibody cell lines, the sample in the receptacle will contain cells which have settled at the bottom of the receptacle. By placing the pipette tip well above the bottom of the receptacle, the sample aspiration step can be carried out without disturbing the cells in the receptacle and thereby drawing them into the sample which is being transferred. The method also increases the accuracy and precision of the system by placing the pipette at a minimum or near-minimum depth of the cell, and allowing material which would otherwise cling to the outside of the tip to be slowly drawn off as the sample is aspirated.

In FIG. 4, which illustrates meniscus-tracking in a sample dispensing operation, liquid level $l_1$ represents the initial meniscus level, and $l_2$, that meniscus level which results when a selected quantity of liquid is dispensed. A selected offset distance o is added to $l_2$ to produce $l_3$, the calculated position of the tip in the dispensing operation. As indicated above, the offset distance o is preferably selected such that at the end of the dispensing step, the final liquid drip which may cling to the lower end of the tip is in contact with the upper liquid surface and drawn off onto the sample by surface tension forces. This feature increases the accuracy of the system in that substantially all of the liquid in the pipette is dispensed into the receptacle. Removing the drip also minimizes cross contamination of receptacles caused by drips falling into adjacent receptacles.

The invention further includes a volume-correction feature which will now be described with reference to the control of stepper motor 52 in device 10. The volume-correction feature is best understood by considering the volume control mechanism in unit 26 as composed of two separate features: a basic volume control feature which operates, in accordance with the prior art, to transfer liquid volumes accurately only within a relatively narrow volume range, and a volume-correction feature which reduces transfer volume errors inherent in the basic feature, particularly at lower and higher transfer volumes.

The basic volume control feature functions typically according to an assumed linear relationship between the extent of plunger movement in a pipette, and the volume of liquid which is withdrawn into or dispensed from the pipette. This relationship is illustrated by the dash-dot line in the graph in FIG. 10, which shows that with an increasing number of steps of motor 52 (which controls the position of actuator bar 48), an increasing volume of liquid is withdrawn into or dispensed from the tips. The line is established by determining the number of motor steps required to effect transfer of a specified intermediate-volume amount of liquid, typically either 50 or 100 $\mu l$, and extrapolating through the 0 point on the graph. The characteristics of liquid transfer operations based on this linear relationship can be seen from the data in Table I below, which compares specified and actual amounts of volume transferred by the device at several volumes between 2 and 200 $\mu l$.

TABLE I

| Specified Volume ($\mu l$) | Actual Volume ($\mu l$) |
|---|---|
| 2 | 0.09 |
| 5 | 3.31 |
| 10 | 8.65 |
| 50 | 49.95 |
| 100 | 101.76 |
| 200 | 206.08 |

As seen from the data, the basic volume control mechanism seriously underestimates the number of motor steps required to transfer relatively small volumes (<10 $\mu l$) and overestimates at large volumes.

As mentioned above, the volume underestimation effects observed above are due, in part, to "play" or slack in the mechanical linkage between motor 52 and the actuator bar, and to non-linearity in the relationship between initial plunger movement and initial changes in the pressure within the tip. The latter problem is particularly serious where the sample to be dispensed is fairly viscous and poorly drawn into the tip under small-volume conditions of only slight pressure differential across the tip opening.

Figure 9:
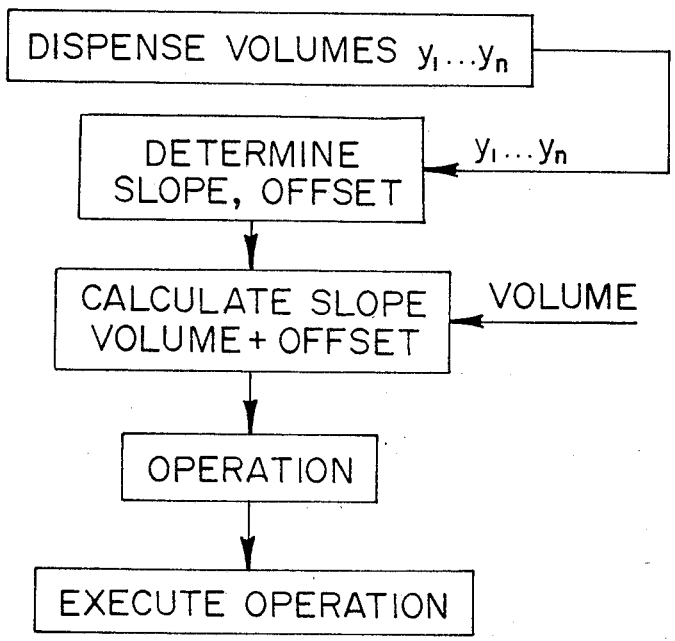
FIG. 9 is a flow diagram showing operation of a volume-correction feature forming part of the invention.
Figure 10:
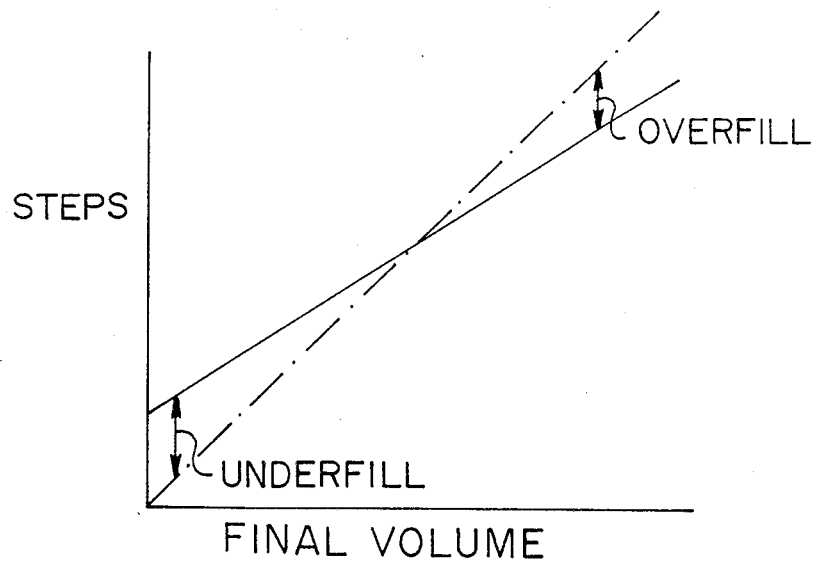
FIG. 10 is a plot showing the relationship between liquid volume transferred, as a function of stepper motor steps, before (dash-dot line) and after (solid line) volume correction according to the invention.

The novel volume-correction feature of the present invention will now be considered with reference to FIGS. 9 and 10. As a first step in practicing this aspect of the invention, actual volumes which are dispensed, at a number of different specified volumes, are determined, yielding data of the type shown in Table I. The relationship between transferred volume and the number of steps of motor 52 is then refined by representing the actual transferred volume (designated y) as an Nth degree polynomial expression which is a function of a specified volume, designated x. The first degree polynomial would be $y=ax+b$, the second degree polynomial, $y=ax^2+bx+c$, and so forth. The polynomial coefficients, a, b, c, ..., are determined from measured volumes of y taken at different specified volumes of x. At least two measured y values are needed to determine the coefficients in the first degree polynomial, three measured values for the second degree polynomial and so forth. In one exemplary embodiment, which will be described herein, the polynomial is a first degree expression, and the a and b coefficients are solved by a simple calculation which uses two measured values of y, or by a closest fit calculation which utilizes more than two and preferably four or five measured values. For purposes of the present illustration, it is assumed that the first degree polynomial is solved, for a and b coefficients, by y values obtained at x values of 2 and 200 $\mu l$. Using the values shown in Table I, values of $a=1.4$ and $b=-2$ are obtained.

The corrected relationship between actual volume dispensed and stepper motor step number is now determined from the rearranged polynomial expression $x=y/a-b/a$, where a and b have the values determined from the equation above and x now designates the corrected transferred volume, expressed in terms of stepper motor step number. This equation for x is shown in solid line in FIG. 10. The line has a slope of $1/a$ and a y-axis intercept of $-b/a$.

From the foregoing discussion, it can be appreciated that the solid line curve represents the corrected approximation of the relationship between volume transfer and stepper motor step number, based on experimentally measured values. The y-intercept of the line represents the offset correction in stepper motor step number needed to overcome the "play" in the system, at the zero-volume point. At increasing volumes, the amount of correction needed to compensate for the play becomes progressively less up to the point of intersection of the two lines, and at greater volume it is seen that the corrected volume acts to reduce the amount of overfill produced by the basic volume feature.

The calculations just outlined are represented in the first two boxes in the flow diagram in FIG. 9, showing the determination of a number of actual volumes $y_1 \ldots y_n$, and the calculation of slope and offset values from the polynomial coefficients. From the rearranged equation, and using a specified volume read by the microprocessor and stored in a volatile memory, the corrected position of the plunger is determined, as indicated in the next box down in FIG. 9, from the slope of corrected-volume line. The calculated step number is then used in the execution step to activate motor 30 to produce the corrected volume transfer operation.

Under normal conditions, volume-correction slope and offset values are determined (recalibrated) only periodically—typically every month or so. Recalibrating the volume-correction values corrects for drift in the device system due to increased "play" in the system, but typically such drift is negligible from day to day. It may, however, be useful to recalibrate the volume-correction values when new samples to be handled have significantly different viscosities than those used in making the existing calibration or when the pipette tips have different volumes than those originally used.

The basic volume control feature in microprocessor 82 is also referred to herein as signal means for supplying one of a preselected number of digitized impulses to the plunger step motor to cause the plunger to dispense an actual liquid volume which approximates a specified amount of liquid transferred. This signal means is represented by the uppermost box in FIG. 9 which is intended to include a microprocessor capability for calculating the number of stepper motor pulses based on the dashed-dot line in FIG. 10. The volume-correction feature just described, which is used for correcting the number of impulses supplied to the plunger motor to reduce the difference between the specified and actual amounts of transferred liquid, is also referred to herein as volume-correction means. The volume correction means is indicated generally by the middle two boxes in FIG. 9. The correction means includes input means, represented by the second box down in FIG. 9, for receiving information about the actual amounts of liquid dispensed at different specified volumes, and calculating means which uses such information for producing such correcting. The construction and programming of a microprocessor, such as the microprocessor in unit 26, to include such signal means, volume correction means, input means and calculating means are within the ability of one skilled in the art.

Using a volume correction feature based on a first-order polynomial whose coefficients were calculated as above, actual corrected volumes corresponding to the several specified volumes ranging from 2 to 200 $\mu$l which are indicated at the left in Table II were measured.

TABLE II

| Specified Volume ($\mu$l) | Corrected Volume ($\mu$l) |
| --- | --- |
| 2 | 2.18 |
| 5 | 5.07 |
| 10 | 10.00 |
| 50 | 49.89 |
| 100 | 99.86 |
| 200 | 200.10 |

As seen from the data in the table, the volume-correction feature gave very close approximations of the specified volumes. In particular, the data show that device 10 can now be operated with high accuracy over a wide volume handling range, in this case, the range between 2 and 200 $\mu$l.

Another improved feature in device 10 is aimed at producing more complete liquid removal from a receptacle, such as the one shown in FIG. 5, in liquid handling operations where it is desired to transfer substantially all of the liquid from that receptacle. Under ordinary operating conditions, where the pipette tip is positioned centrally within the receptacle, as shown in FIGS. 3 and 4, even after all of the liquid has been withdrawn from the central region of the receptacle, there will remain a ring or bead of liquid around the lower edge of the receptacle, as indicated. In order to remove this peripheral bead material, the table is shifted relatively with respect to the pipette tips by suitable actuation of motor 20, to place the pipette tip first at the position shown in dotted lines in FIG. 5 to remove the beaded material near the left hand side of the receptacle and following this, to place the pipette in the position shown in solid lines to pick up material from the right hand side of the receptacle. The table movement operation is carried by an electronic control program forming part of the microprocessor in unit 26.

To better illustrate the novel features of the present invention, a complete liquid-handling operation for transferring a selected quantity of liquid from a sample in one receptacle, such as receptacle 84, to another receptacle in a different row in the tray will be described. The microprocessor is initially programmed with information about the start volume in each receptacle and the amount of liquid to be transferred. From this information, the microprocessor computes successive table positions for carrying out the transfer, pipette tip positions for withdrawing and dispensing the preselected amount of liquid, and the corrected plunger positions for transferring the specified amount of liquid. If necessary, the volume-correction slope and offset values may be recalibrated for the specific sample viscosity or pipette volume.

The table is then moved, under the control of motor 20, to position receptacle 87 directly beneath the pipettes, and the head assembly is moved downwardly, under the control of motor 30, to place the lower end of each pipette tip at a position which is at or just below the liquid line which will result when the specified liquid volume is removed from the receptacle. The plunger assembly is now raised, under the control of motor 52, a distance which effects withdrawal of the corrected volume from the receptacle.

To transfer the withdrawn sample to the next receptacle, the head assembly is raised, the table is shifted to position receptacle 86 below the pipettes, as seen in FIG. 1, and the head assembly is then lowered to place the lower end of each pipette tip at or slightly above the meniscus level which will result after liquid is dispensed from the pipettes. The liquid handling operation is completed by activating the plungers to dispense liquid carried in the pipettes and raising the head assembly to allow the table to be moved to the next desired position.

From the foregoing, it can be appreciated how the present invention contributes to improved accuracy in a liquid-handling device. The meniscus tracking feature, as noted above, increases volume transfer accuracy by reducing the amount of extraneous material carried on or in the pipette tips and, in a sample containing settled cells, allows for the transfer of an upper soluble liquid sample which is free of the cells. The meniscus tracking feature, as it functions in liquid dispensing step, also reduces the risk of contamination of other samples during the liquid handling operation.

The volume-correction feature of the invention allows accurate liquid transfer of both small and large liquid volumes, effectively increasing the range of liquid volumes which can be transferred in an automated fashion. In the specific example described herein, volumes ranging from 2 µl to 200 µl can be transferred with great accuracy. The feature, which provides a volume correction for a basic volume control mechanism, allows the device to be calibrated periodically to adjust for increasing amounts of play in the mechanical linkage, for different sample viscosities and, for different-volume tips, all of which can produce variations in the relationship between transferred volume and number of steps in the stepper motor controlling liquid withdrawal and dispensing operations.

A novel-table shifting feature described herein permits substantially all of the liquid sample to be withdrawn from a flat-bottomed receptacle, where desired.

While the invention has been described with respect to particular embodiments, and in association with one type of liquid handling device, it will be appreciated that various changes and modifications in the invention, may be made without departing from the spirit of the invention.

We claim:

1. In an automatic liquid handling device in which a pipette tip having a lower end is moved into a receptacle, to allow a preselected quantity of liquid to be withdrawn from, or dispensed into the receptacle,
   calculation means for calculating a final volume level based upon a starting volume and a transfer volume to be either aspirated or dispensed and for calculating a final tip position based upon said final volume less an immersion distance if an aspiration transfer is to be performed or plus an offset distance if a dispense operation is to be performed and for generating control signals;
   positioning means operatively connected to said control signals for positioning the tip's lower end at a selected level calculated by said calculation means above or below the liquid meniscus which results in the receptacle when such selected quantity of liquid is withdrawn from or dispensed into the receptacle.

2. The device of claim 1, wherein said positioning means is operable to position the tip's lower end at a selected level which is on or immersed up to about 100 mils below such meniscus, when such preselected quantity of liquid is withdrawn from the receptacle, at a selected level which is on or offset about 100 mils above such meniscus, when such preselected quantity of liquid is dispensed into the receptacle.

3. The device of claim 1, wherein calculation means also functions to check the final calculated tip position against a lower threshold constant and causes said positioning means to move said tip to said threshold level if the final tip position is below the threshold level and to move said tip to its final calculated position if same is above said threshold level.

4. The device of claim 3, wherein the threshold level achievable is spaced from the bottom of such receptacle.

5. In an automatic liquid handling device which comprises a pipette assembly composed of a pipette having a tip with a lower end, plunger means moveable in upward and downward directions to withdraw liquid into and dispense liquid from the pipette, respectively, and a plunger stepper motor which is responsive to externally supplied digitized impulses to move the plunger in upward or downward directions to withdraw liquid into and dispense liquid from the pipette, respectively, and shifting means operatively connected to the pipette assembly for shifting the latter into a receptacle, to allow liquid in the receptacle to be withdrawn into the pipette, in response to upward movement of the plunger means,
   positioning means operatively connected to the shifting means for positioning the tip's lower end at a selected level within the receptacle which is less than about 100 mils from the liquid meniscus which forms in the receptacle when such preselected quantity is withdrawn from or dispensed into the receptacle,
   signal means for supplying one of a preselected number of such impulses to the plunger step motor to cause the plunger to transfer an actual liquid volume which approximates a specified amount of liquid to be transferred, and
   volume-correction means for correcting the number of such impulses supplied to the plunger step motor to reduce the difference between such specified and actual amounts of transferred liquid.

6. The device of claim 5, wherein said signal means is constructed to produce an actual amount of dispensed liquid which is substantially identical to one such specified volume, and at specified volumes below and above the one specified volume, produces actual amounts of dispensed fluid which are less than and greater than, respectively, the corresponding specified volumes.

7. The device of claim 5, wherein said correction means includes input means for receiving information about the actual amounts of liquid dispensed at different specified values, and calculating means which uses such information for producing such correcting.

8. A method for transferring a selected volume of liquid from one receptacle to another comprising
   determining the liquid level which will result in the one receptacle when such volume is removed therefrom,
   positioning the lower end of a pipette tip in the one receptacle at or within about 100 mils below such level,
   withdrawing such volume from the one receptacle, and
   dispensing such withdrawn liquid into the other receptacle.

9. The method of claim 1, which further includes determining the liquid level which will result in the other receptacle when such withdrawn volume is dispensed therein, and positioning the lower end of the pipette tip in the other receptacle at or within about 100 mils above such level.

10. The method of claim 8, wherein said withdrawing is accomplished by an automated device which produces a detectable error between the actual and the specified amounts of liquid transferred from one receptacle to another receptacle, and said method further includes representing the actual amount of liquid transferred by such automated device as a polynomial expression whose variable terms represent corresponding specified amounts of liquid withdrawn, using data relating actual transfer volumes to the corresponding specified transfer volumes to solve for the coefficients in the polynomial expression, using the solved expression to determine a correction factor between actual and specified amounts of liquid to be withdrawn, and applying the correction factor to the automated device to correct the amount of liquid transferred by such automated device to reduce such error.

11. A method for reducing the difference between actual and specified amounts of liquid being transferred by an automated device from one receptacle to another comprising representing the actual amount of liquid transferred by such automated device as a polynomial expression whose variable terms represent corresponding specified amounts of liquid withdrawn, using data pertaining to actual transfer volumes to solve for the polynomial expression, using the solved expression to determine a correction factor between actual and specified amounts of liquid to be withdrawn, and applying the correction factor to the automated device to correct the amount of liquid transferred by such automated device to reduce the difference between actual and specified liquid amounts.

12. The device of claim 1, wherein said positioning means includes a horizontally translatable table capable of shifting relatively with respect to the pipette tip so as to place the tip near one side of the receptacle and then to place the tip near the other side of the receptacle, so that the liquid is substantially completely withdrawn from the receptacle.

13. The method of claim 8, wherein said withdrawing is accomplished by shifting a horizontally translatable table capable of shifting relatively with respect to the pipette tip so as to place the tip near one side of the receptacle and then to place the tip near the other side of the receptacle, so that the liquid is substantially completely withdrawn from the first receptacle.

* * * * *